(12) United States Patent
Packman et al.

(10) Patent No.: US 8,653,481 B2
(45) Date of Patent: Feb. 18, 2014

(54) UV DISINFECTANT DEVICE FOR BIOFILM FLOW CELL

(75) Inventors: Aaron I. Packman, Evanston, IL (US); Wei Zhang, Evanston, IL (US); Tadas Sileika, Northbrook, IL (US)

(73) Assignee: Northwestern University, Evanston, IL (US)

( * ) Notice: Subject to any disclaimer, the term of this patent is extended or adjusted under 35 U.S.C. 154(b) by 356 days.

(21) Appl. No.: 12/924,440

(22) Filed: Sep. 27, 2010

(65) Prior Publication Data

US 2011/0081274 A1    Apr. 7, 2011

Related U.S. Application Data

(60) Provisional application No. 61/277,659, filed on Sep. 28, 2009.

(51) Int. Cl.
*G01N 23/00* (2006.01)
*A61N 5/00* (2006.01)
*G21G 4/00* (2006.01)

(52) U.S. Cl.
USPC .... 250/461.1; 99/451; 250/493.1; 250/492.1; 250/455.11

(58) Field of Classification Search
USPC ............... 99/451; 250/493.1, 492.1, 455.11; 210/748.1; 422/1, 24; 435/173.1
See application file for complete search history.

(56) References Cited

U.S. PATENT DOCUMENTS

| | | | | |
|---|---|---|---|---|
| 3,894,236 A | * | 7/1975 | Hazelrigg | 250/435 |
| 2005/0269521 A1 | * | 12/2005 | Zagrobelny | 250/435 |
| 2007/0272877 A1 | | 11/2007 | Tribelsky | 250/43 |
| 2008/0095661 A1 | * | 4/2008 | Kohler | 422/20 |
| 2008/0290045 A1 | * | 11/2008 | Robinson et al. | 210/748 |

OTHER PUBLICATIONS

Feb. 2009, Poster presented at Am. Assoc. for the Advancement of Science (AAAS) 2009.
Jun. 2009, Poster presented at Am. Society of Microbiology 2009.

* cited by examiner

*Primary Examiner* — Monzer R Chorbaji

(57) ABSTRACT

A UV (ultraviolet) light disinfectant apparatus useful with a biofilm flow cell for in-line, non-invasive disinfecting of medium flow to and from the flow cell is provided. The disinfectant apparatus includes a UV chamber having a UV light source therein and one or more UV light-transmissive tubes that extend through the UV chamber and through which the fluid medium flows through the UV chamber for exposure to UV light for purposes of disinfectation.

8 Claims, 6 Drawing Sheets

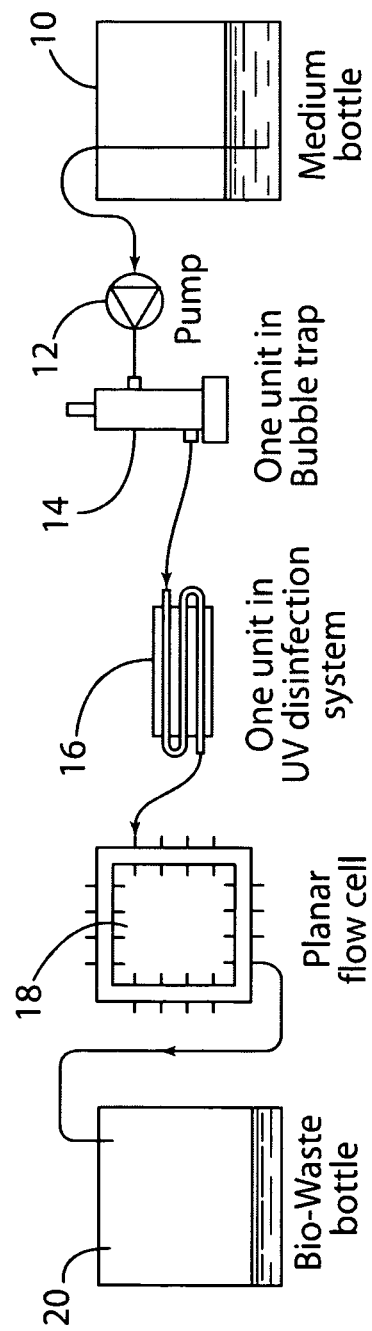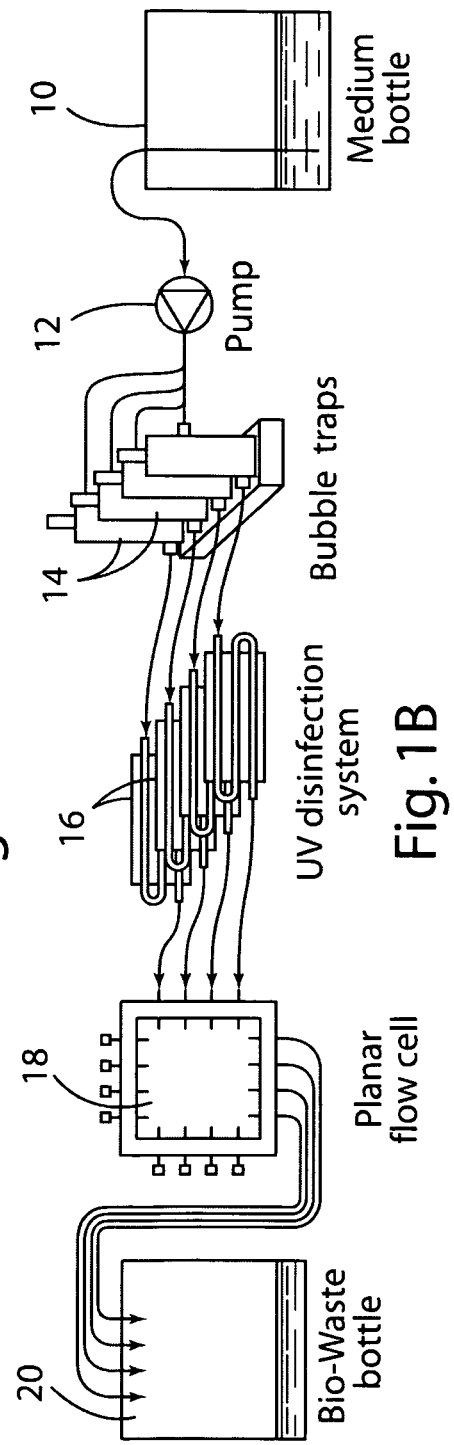

UV DISINFECTANT DEVICE FOR BIOFILM FLOW CELL

This application claims benefits and priority of provisional application Ser. No. 61/277,659 filed Sep. 28, 2009, the disclosure of which is incorporated herein by reference.

CONTRACTUAL ORIGIN OF THE INVENTION

This invention was made with government support under Grant No. CBET-0730976 awarded by the National Science Foundation. The Government has certain rights in the invention.

FIELD OF THE INVENTION

The present invention relates to a UV (ultraviolet) light disinfectant apparatus useful with a biofilm flow cell or other bioreactor for in-line, non-invasive disinfecting of influent medium to the biofilm flow cell.

BACKGROUND OF THE INVENTION

Bioflim flow cells (biofilm culturing devices) have been used to grow surface-attached microbial communities (biofilms) under pre-specified, complex flow conditions including both spatial and temporal variability in influent flows, nutrient levels, substrates, etc. as a result of workers recognizing that microbial communities on interfaces, termed biofilms, are extremely important in a wide variety of environmental, engineered, and biomedical uses.

Biofilms are responsible for more than half of microbial infections, and these infections are highly problematic because cells in bioflims are typically more than 500 times resistant to antimicrobial therapy than planktonic cells. Moreover, bioflims play a significant role in global biogeochemical cycling and in bioreactor systems by changing properties of interfaces, consuming nutrients, degrading hazardous organic compounds, and immobilizing metals.

Normally, in-line filters or flow breaks are used to prevent growth of bacteria upstream of laboratory culturing devices, such as flow cells. However, these sorts of in-line devices are prone to clogging because of either microbial colonization or deposition of material from the influent growth medium. This normally restricts the duration of laboratory experiments involving biofilms to a few days, or a week at most. Such filters or in-line controls have been found to adversely affected flow conditions, especially when used in connection with planar (two-dimensional) flow cells.

SUMMARY OF THE INVENTION

The present invention provides an in-line, non-invasive UV light disinfectant apparatus and method useful with a biofilm flow cell or other bioreactor for in-line, non-invasive disinfecting of influent medium to the biofilm flow cell.

In an illustrative embodiment of the invention, the UV light disinfectant apparatus comprises a UV chamber having a UV (ultraviolet) light source therein and one or more UV light-transmissive tubes, such as capillary tubes, that extend through the UV chamber and through which the influent medium flows through the UV chamber for exposure to UV light. The apparatus includes light reflecting walls that define the UV chamber to expose the influent medium in the capillary tubes to direct and reflected UV light.

A plurality of capillary tube assemblies can be employed above and below the UV light source with each capillary tube assembly being configured to provide multiple passes of the influent medium through the UV chamber. For example, each capillary tube assembly can include multiple glass capillary tubes and one or more U-bend connector tubing sections that redirect the influent medium to flow back through the UV chamber in the opposite direction from the direction in which the fluid medium entered the UV chamber.

The present invention envisions a disinfection system including a combination of a biofilm reactor, such as a biofilm flow cell, placed in-line with the inflow tubing and optionally outflow tubing that goes to/from the flow cell. The flow cell receives the influent medium from the UV disinfectant apparatus described above that is effective in preventing growth of bacteria (non-invasively kill bacteria) without inducing any disruption of the influent (inflow) or effluent (outflow). The UV disinfection system is effective to non-invasively kill bacteria in the inflow and outflow tubing. The in-line UV disinfection system is advantageous to enable continuous operation of small-scale, flow-through microbial culture systems. No filters or similar devices are required such that precise flow control can be maintained to the flow cell.

Other advantages of the present invention will become more readily apparent from the following drawings taken with the following detailed description.

BRIEF DESCRIPTION OF THE DRAWINGS

FIG. 1A is a schematic illustration of a disinfection system including a source of an influent fluid medium (e.g. a fluid growth medium), an influent medium pump, a bubble trap, a UV disinfection apparatus pursuant to the invention, a planar biofilm flow cell, and a bio-waste (effluent) bottle.

FIG. 1B is a schematic illustration of a disinfection system including an influent fluid medium (e.g. a fluid growth medium), an influent medium pump, multiple bubble traps upstream of and communicated to respective UV disinfection apparatus pursuant to the invention, multiple planar flow cells supplied with the influent medium via a respective UV disinfection unit, and bio-waste (effluent) bottle.

DETAILED DESCRIPTION OF THE INVENTION

Figure 2B:
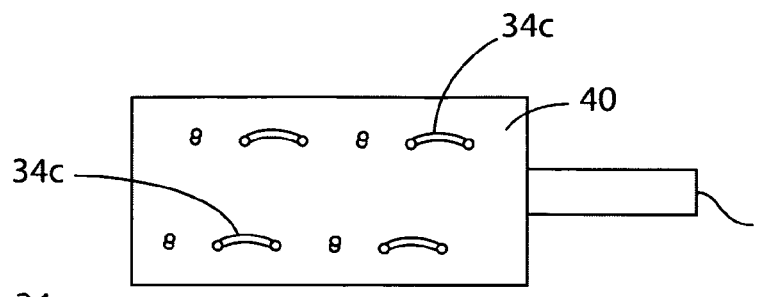
FIGS. 2B and 2C are views of the ends of the UV chamber showing the U-bend connector tubing sections of the capillary tube assemblies to redirect the influent medium to flow back through the UV chamber in the opposite direction from the direction in which the fluid medium entered the UV chamber.

Referring to FIGS. 1A and 1B, the present invention provides an in-line, non-invasive UV light disinfectant apparatus and method useful with a biofilm flow cell or other bioreactor for in-line, non-invasive disinfecting of influent medium supplied to the biofilm flow cell. For example, FIG. 1A schematically illustrates a disinfection system including a source of an influent fluid medium (e.g. a bottle containing fluid growth medium) 10, an influent medium pump 12, a bubble trap 14, a UV disinfection apparatus 16 pursuant to the invention, a bioreactor 18 such as planar biofilm flow cell, and a bio-waste (effluent) bottle 20. FIG. 1B is a similar system but includes multiple bubble traps 14 upstream of respective UV disinfection apparatus 16 pursuant to the invention, and multiple planar flow cells 18 supplied with the influent medium via a respective UV disinfection unit 16.

Figure 2A:
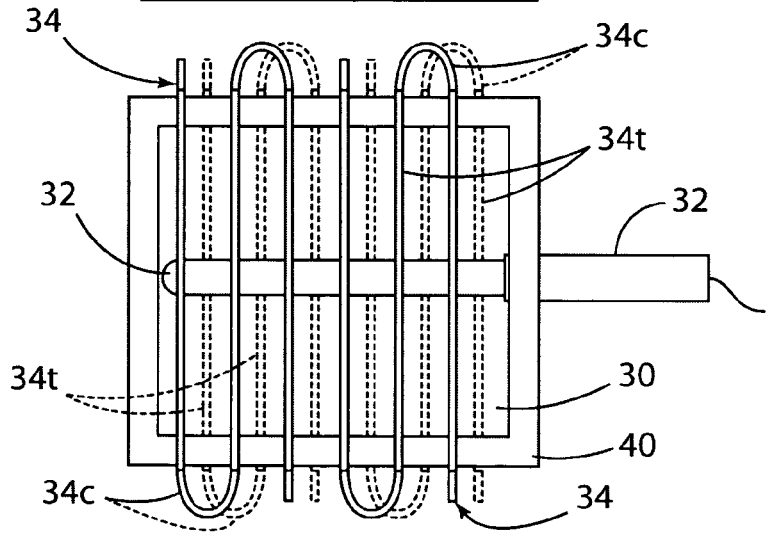
FIG. 2A is a schematic top view of a UV disinfection apparatus with the top cover removed showing the UV chamber and a plurality of light-transmissive capillary tube assemblies having glass capillary tubes extending through the UV chamber and in which influent growth medium flows for exposure to direct and reflected UV light from the UV light source residing in the UV chamber. Two pairs of capillary tube assemblies are disposed above and and two pairs below the UV light source in the UV chamber.
Figure 2C:
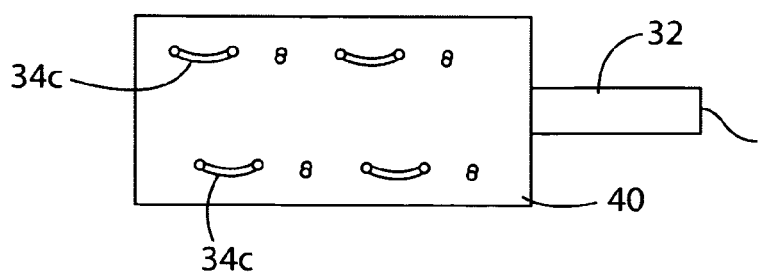
Figure 3A:
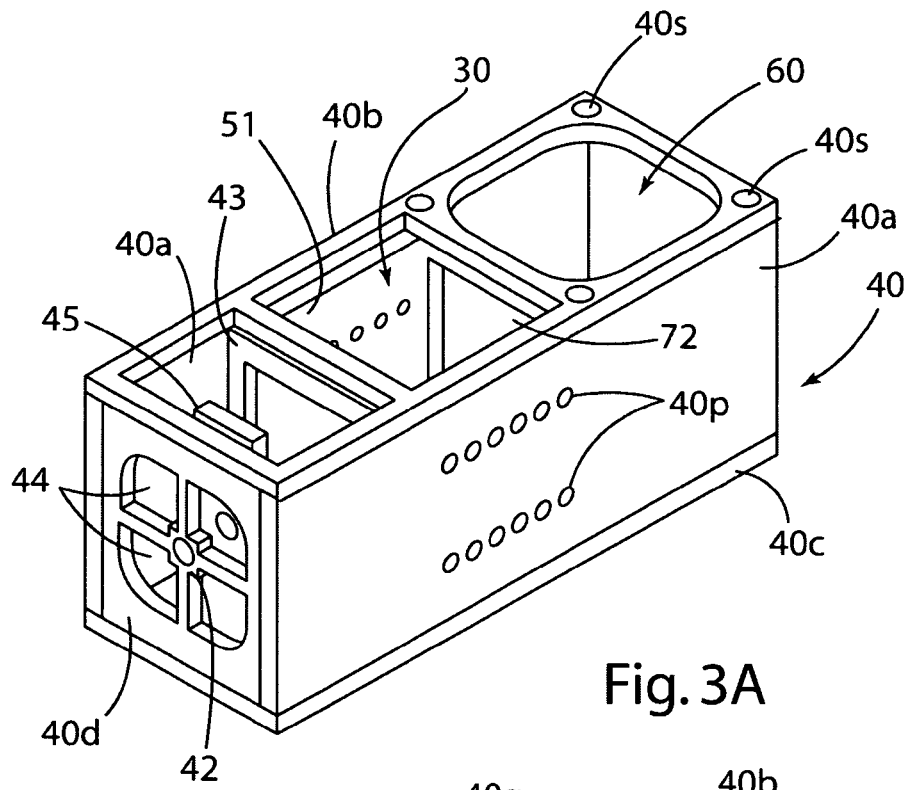
FIGS. 3A and 3B are perspective views of the housing forming the UV chamber of the disinfection apparatus showing different viewing directions.
Figure 3B:
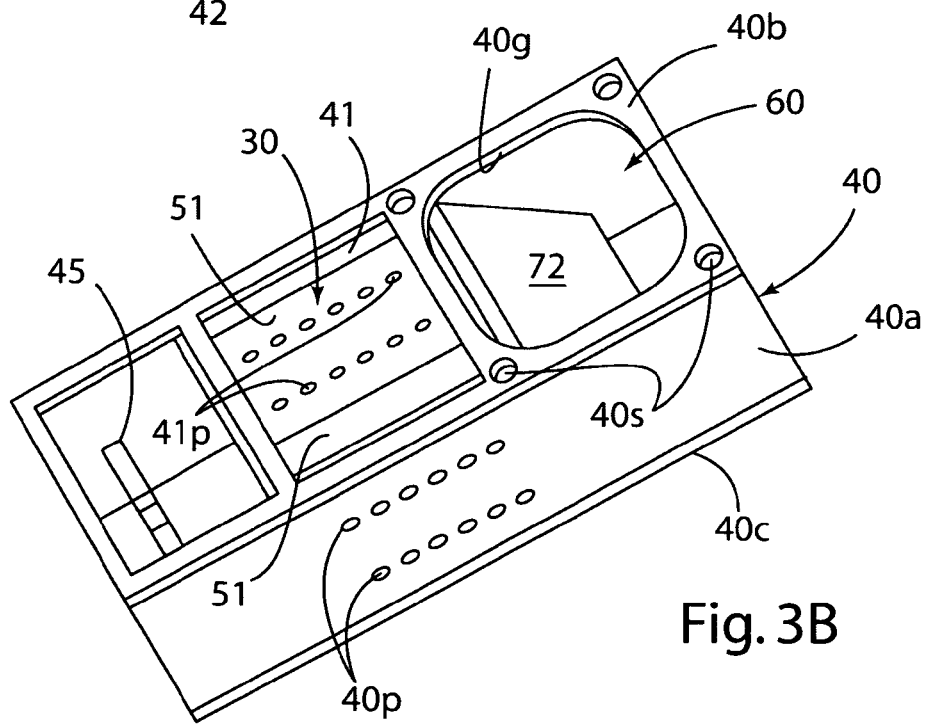
Figure 4A:
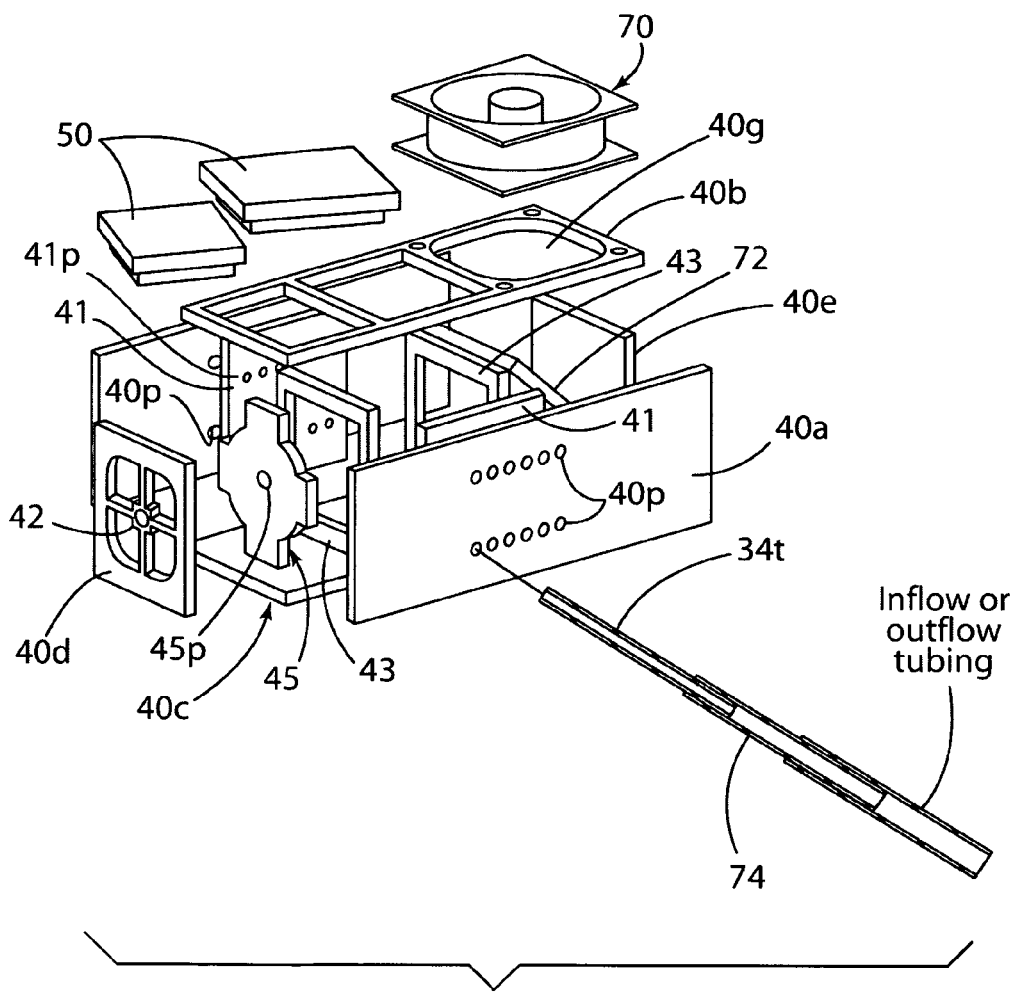
FIGS. 4A and 4B are exploded views of the housing forming the UV chamber of the disinfection apparatus from different viewing directions. The capillary tube, tubing reducer fitting, and inflow or outflow tubing are shown enlarged beyond their normal size for clarity.
Figure 4B:
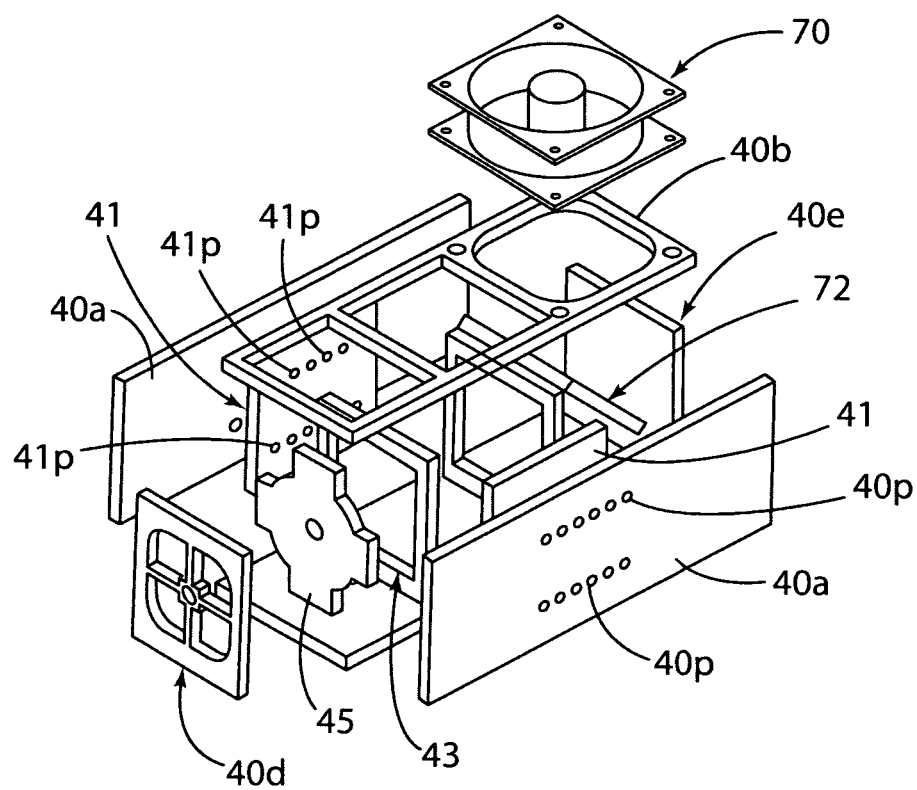

In an illustrative embodiment of the invention shown in FIGS. 2A-2C; 3A, 3B; and 4A, 4B, the UV disinfectant apparatus 18 comprises a UV chamber 30 having a UV light source 32 therein and one or more UV light-transmissive tubes 34t that extend through the UV chamber 30 and through which the influent medium flows through the UV chamber for exposure to UV light.

The UV chamber 30 is formed in a housing 40 having a pair of upstanding sidewalls 40a, an apertured top wall 40b, a solid bottom wall 40c an apertured end wall 40d, and solid end wall 40e. An apertured divider or support frame 43 is provided on opposite ends of the UV chamber. End wall 40d includes a cylindrical pen light support hub 42 that receives the elongated UV light source 32 in the form an elongated UV pen light 32 and air inlet apertures 44. The pen light extends through a passage 45p of a pen light support block 44 attached in the UV chamber and then into the UV chamber 30, FIGS. 2A, 2B, 2C. UV light can have a wavelength in the range of about 10 nm to about 400 nm for purposes of illustration and not limitation. The block 44 has cut-outs that define air inlet paths that communicate with inlet apertures 44 of the end wall 40d. End wall 40e is solid. One or more covers 50 (two shown) is/are disposed on top of the sections of the housing 40 to close off the UV chamber 30 as shown.

For purposes of illustration and not limitation, the UV pen light can comprise a Pen-Ray® Mercury lamp (254 nm wavelength) from McMaster Carr (part no. 90-0012-01). The walls and covers 50 of the housing 40 can be made of 0.25 inch thick acrylic plates with the walls glued or otherwise fastened together. The walls and cover(s) of the housing are painted with flat, black acrylic paint to make them non-transmissive to light. Also, the walls and covers can be made of 0.25 inch thick black, opaque acrylic, which does not have to be painted, as it already blocks UV light (McMaster Carr part no. 8650K321).

The inside surfaces of the UV chamber 30 are lined with light reflective material 51, such as Mylar film or laser-cut mirrored acrylic material (McMaster Carr part no. 1518T52), in order to reflect the UV light so as to expose the influent medium in the capillary tubes 34t to direct and reflected UV light for increased efficiency in killing bacteria. The inner surfaces of the bottom wall, sidewalls, and end walls of the housing 40 can be lined to this end. The inner surface of the covers 50 can be lined to this same end. The reflective material is laser-cut (using a computer-controlled laser cutting machine) to match the dimension of the internal surfaces and to provide additional reflection of scattered light. Also, the inner surfaces of the reducer plates 41 described below are lined to this end as well. The reflective material is laser-cut to match the dimensions of the reducer plates. The objective is to make any internal surface, except holes and cut-outs, exposed to UV light capable of reflecting light.

An air outlet chamber 60 is formed in the end region of the housing closed off by end wall 40e. An exhaust fan 70 is mounted on the top wall 40b of the housing 40 above the chamber 60 using four fan mounting screw holes 40s to draw air through end wall air inlets 44, through the UV chamber 30 and out of the chamber 60 as directed by a fixed diagonal air deflector 72 to control temperature within the UV chamber 30 in a desired range. The top housing wall 40b includes an aperture 40g to provide an air flow opening out of the chamber 60. The other two apertures shown in the housing top wall 40a are access openings, which are closed off by the covers 50. The covers correspond to the dimensions of the respective apertures. when they are attached on top of the housing.

The sidewalls 40a of the housing include holes 40p that receive the larger outer diameter inflow tubing from a respective bubble trap 14 and outflow tubing to the respective flow cell 18. Reducer plates 41 are disposed on and fastened by adhesive or other means to the inner side of each sidewall 40a and include holes 41p of smaller outer diameter than hole 40p to receive tubing reducer fittings 74 that have a smaller inner diameter to receive the ends of the tube assemblies as shown best in FIGS. 2A, 2B, and 2C where a pair of capillary tube assemblies 34 are shown mounted in the upper holes 41 p and another pair of capillary tube assemblies 34 are mounted in the lower holes 41p so as to reside above and below the UV pen light 32 in the UV chamber 30 and extending generally perpendicular thereto. The ends of the capillary tubes 34t can be inserted into a respective tubing reducer fitting 74, which has an inner diameter that matches the outer diameter of the capillary tube 34t and an outer diameter matching the inner diameter of the respective inflow or outflow tubing as appropriate. The reducer fittings 74 aid in preventing the escape of scattered UV light as well as provide mechanical support for the capillary tube assemblies.

Each capillary tube assembly 34 comprises three transparent glass capillary tubes 34t connected at ends by two flexible U-bend connector tubing 34c as shown in FIGS. 2A, 2B, 2C. For purposes of illustration and not limitation, the glass capillary tubes 34t can comprise 0.4 mm ID/75 mm long glass capillary tubes available from Drummond Scientific (part no. 1-000-800). The flexible connector tubing 34c can comprise 0.094 inch/0.156 inch OD C-Flex tubing available from Cole-Parmer (part no. 06422-03). The capillary tubes 34 have their ends received in the reducer fittings 74, FIGS. 2A, 2B, 2C which are disposed in the holes 40p so as to mount the capillary tubes 34t to extend across the UV chamber 30. The reducer fittings are available from Cole-Parmer (part no. 6365-50).

The two U-bend connector tubing sections 34c of each capillary tube assembly 34 redirect the influent fluid medium to flow back through the UV chamber 30 in the opposite direction from the direction in which the fluid medium entered the UV chamber. Referring to FIGS. 2A, 2B, and 2C, it is apparent that each capillary tube assembly 34 provides three passes of the influent medium through the UV chamber 30, although the capillary tube assemblies can have other configurations to provide fewer or more passes through the UV chamber.

After the capillary tubes 34 are assembled on the housing, the covers 50 are attached by screws or other releasable fastening devices with its middle light reflective section overlying the UV chamber 30. A protective rubber sheet can be cut with appropriate apertures and fitted between the covers 50 and the top wall 40a of the housing.

Figure 5:
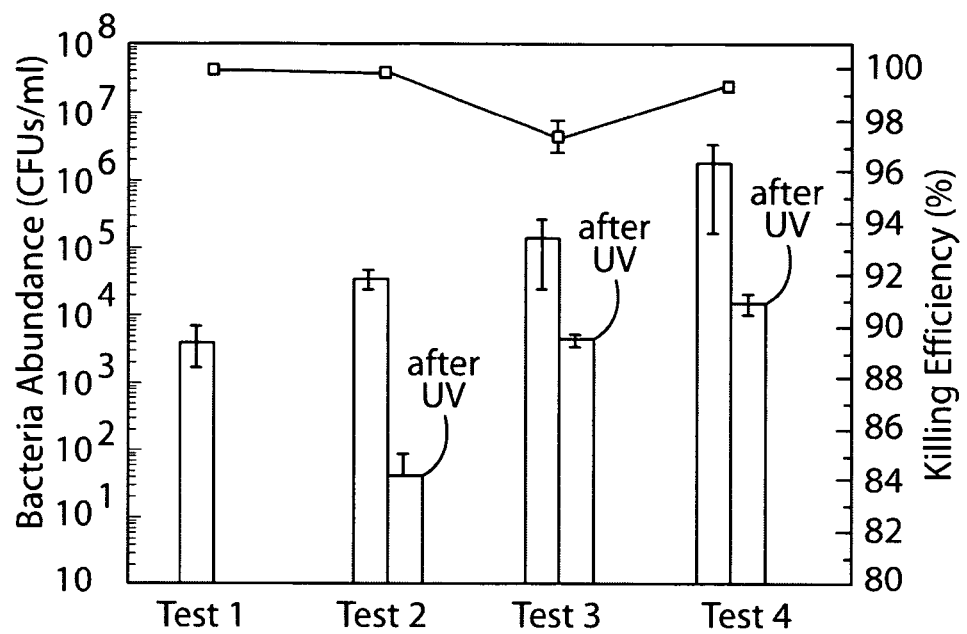
FIG. 5 is a graph depicting bacteria abundance and killing efficiency for tests 1, 2, 3, and 4.

FIG. 5 illustrates disinfection efficiency of the in-line UV disinfection system. in continuous experiments ran in parallel, one with a UV disinfection apparatus as described above, and the other one without, as a negative control. Results of FIG. 5 are presented for four different initial concentrations of inoculated cells. Killing was very efficient in all cases using UV, with 100% killing found for influent concentrations on the order of $10^3$-$10^4$ CFU/ml. After five days, bacterial growth was detected in the control, visible biofilm growth inside the upstream tubing and associated clogging. No bacterial growth was detected upstream of the UV apparatus after eleven days of continuous operation. The UV disinfection apparatus was shown to be effective at preventing microbial upstream growth inside the connective tubing. The non-invasive disinfection apparatus provides a means of supporting continuous system operation without the need for disruption of the flow path (i.e., no filters or similar devices are required, so precise flow control can be maintained).

In addition to the research uses, the invention can find use in biofilm control in industrial settings and also in treating biofilm-based infections. As a result, there is a broad applicability for testing devices capable of simulating various environments where biofilms are found in order to evaluate the effectiveness of new biocides and other control measures. In addition, bioreactors are used to achieve desirable chemical transformations in a wide variety of applications, including wastewater treatment, bioremediation, chemical processing, pharmaceuticals, and others.

Although the present invention has been described in connection with certain illustrative embodiments thereof, those skilled in the art will appreciate that changes and modifications can be made thereto within the scope of the invention as set forth in the appended claims.

The invention claimed is:

1. A non-invasive UV light disinfectant apparatus for a fluid medium, comprising a housing having a pair of upstanding end walls, a pair of upstanding sidewalls between the end walls, a bottom wall and an apertured toy wall closed by a cover, a UV chamber formed within the housing between the pair of upstanding sidewalls, one or more capillary tube assemblies that extend through the UV chamber between and supported on the upstanding sidewalls and through which the fluid medium flows through the UV chamber for exposure to UV light, wherein each of the one or more capillary tube assemblies includes multiple UV light-transmissive Hillary tubes extending between the upstanding sidewalls across the UV chamber with open ends of adjacent capillary tubes connected in fluid medium flow relation by a respective U-bend connector tubing that resides outside of the UV chamber and that redirects the fluid medium to flow back through the next adjacent capillary tube in the opposite direction from the direction in which the fluid medium flowed in the preceding adjacent capillary tube, whereby each of said one or more capillary tube assemblies provides multiple passes of the same fluid medium through the UV chamber, and a UV light source disposed on one of the upstanding end walls so as to reside in the UV chamber to expose the fluid medium in the UV light-transmissive capillary tubes to UV light.

2. The apparatus of claim 1 having light reflecting surfaces that define the UV chamber.

3. The apparatus of claim 1 wherein the multiple capillary tubes each comprises transparent glass.

4. The apparatus of claim 1 including a fan disposed on the apertured ton wall outside of the UV chamber to draw air through apertures in one of the end walls, through the UV chamber, and through an air exhaust aperture in the top wall to control temperature in the UV chamber.

5. The apparatus of claim 4 including an air deflector adjacent an end of the UV chamber.

6. The combination of a biofilm reactor that receives the fluid medium from the UV disinfectant apparatus of claim 1.

7. The combination of claim 6 wherein the biofilm reactor is a planar flow cell.

8. The apparatus of claim 1 wherein the open ends of the adjacent capillary tubes are received and supported in respective tubing reducer fittings received in respective holes in the upstanding sidewalls.

\* \* \* \* \*

UNITED STATES PATENT AND TRADEMARK OFFICE
CERTIFICATE OF CORRECTION

PATENT NO. : 8,653,481 B2
APPLICATION NO. : 12/924440
DATED : February 18, 2014
INVENTOR(S) : Aaron I. Packman, Wei Zhang and Tadas Sileka Page 1 of 1

It is certified that error appears in the above-identified patent and that said Letters Patent is hereby corrected as shown below:

In the claims:

Column 5, claim 1, line 33, replace "toy" with --top--.

Column 6, claim 1, line 3, replace "Hillary" with --capillary--.

Column 6, claim 4, line 22, replace "ton" with --top--.

Signed and Sealed this
Twenty-seventh Day of May, 2014

Michelle K. Lee
*Deputy Director of the United States Patent and Trademark Office*